United States Patent [19]

Nelson et al.

[11] Patent Number: 4,742,178

[45] Date of Patent: May 3, 1988

[54] LOW PRESSURE HYDROFORMYLATION OF DIENES

[75] Inventors: Gregory O. Nelson, Kingsport, Tenn.; Thomas J. Devon, Longview, Tex.; Thomas A. Puckette, Longview, Tex.; Jerome L. Stavinoha, Longview, Tex.; Gerald W. Phillips, Longview, Tex.; Jeffrey J. Vanderbilt, Longview, Tex.

[73] Assignee: Eastman Kodak Company, Rochester, N.Y.

[21] Appl. No.: 929,120

[22] Filed: Nov. 10, 1986

[51] Int. Cl.$^4$ .............................................. C07C 45/50
[52] U.S. Cl. ..................................... 568/454; 568/455
[58] Field of Search ........................ 568/454, 455, 494

[56] References Cited

U.S. PATENT DOCUMENTS

| | | | |
|---|---|---|---|
| 2,880,241 | 3/1959 | Hughes | 568/451 |
| 4,507,508 | 3/1985 | Hayden et al. | 568/454 |
| 4,608,443 | 8/1986 | Andrade et al. | 568/454 |

FOREIGN PATENT DOCUMENTS

| | | | |
|---|---|---|---|
| 0094748 | 11/1983 | European Pat. Off. | 568/454 |
| 0201743 | 11/1983 | Japan | 568/454 |
| 0216138 | 12/1983 | Japan | 568/454 |

*Primary Examiner*—Werren B. Lone
*Attorney, Agent, or Firm*—S. E. Reiter; W. P. Heath, Jr.; J. Frederick Thomsen

[57] ABSTRACT

A hydroformylation process for preparing dialdehydes from dienes by contacting a $C_6$–$C_{10}$ diene in a reaction zone at a temperature of from about 20° C. to about 250° C. and a pressure of from about 15 psig to about 800 psig with hydrogen, carbon monoxide, and a catalyst containing rhodium, the ligand having the formula

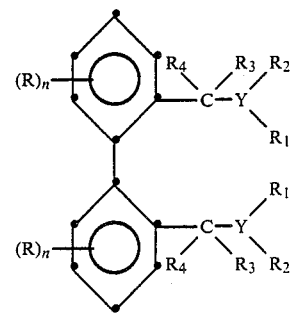

wherein:

n is 1–4;

each R is independently selected from hydrogen, alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each $R_1$ and $R_2$ is independently selected from alkyl, aryl, aralkyl, alkaryl or cycloaliphatic;

each $R_3$ and $R_4$ is independently selected from hydrogen and the $R_1$ substituents; and each Y is independently selected from the elements N, P, As, Sb and Bi.

10 Claims, No Drawings

LOW PRESSURE HYDROFORMYLATION OF DIENES

TECHNICAL FIELD

Ths invention concerns the hydroformylation of dienes employing special catalysts and processes wherein one or more dienes are converted to aldehydes for use as such or for conversion by known methods, to products such as diols and acids. More particularly, the invention concerns the use of ligands especially useful with rhodium for oxo or hydroformylation processes designed for relatively low pressure operation for the preparation of 1,10-decanedialdehyde from 1,7-octadiene in unusually high yields, and the subsequent reduction thereof to 1,10-decanediol, a useful monomer for the preparation of polyester materials. ,cl BACKGROUND ART Several factors indicate that there will be an excess of butadiene available in the future in that many of the products that now utilize butadiene are undergoing very slow growth or are on the decline. In addition, it is predicted that larger amounts of heavier feedstocks will be cracked which will result in a higher percentage of $C_4$'s being produced. One approach to utilizing the butadiene is to envision what chemicals can be made from the first line derivatives of this highly reactive feedstock. The reactant 1,7-octadiene which itself can be synthesized in high yield from butadiene by the process described in U.S. Pat. No. 4,229,606, is used herein for the synthesis of 1,10-decanedialdehyde in 70% yield using low pressure hydroformylation technology. This dialdehyde can be easily hydrogenated to 1,10-decanediol, a useful monomer for condensation polyester polymers. The dienes useful in the present invention include the $C_6$ to $C_{10}$ dienes, particularly 1,7-octadiene, 1,5-hexadiene, and 1,9-decadiene.

The major problem with the hydroformylation of 1,7-octadiene to the desired 1,10-decanedialdehyde is the large number of side products that can result in the hydroformylation of this diolefin compound. The chance for producing a branched dialdehyde product is doubled over the branched yield of the hydroformylation of a straight chain alpha olefin by virtue of having two olefinic sites that have to be hydroformylated at both of the terminal carbons. A comparison of the 1,10-decanedialdehyde yield employing the catalyst of this invention is provided in Table I below against the product yields from other catalyst systems including a triphenylphosphine ligand (TPP) modified rhodium catalyst, a system which is used commercially for the preparation of butyraldehyde product with a high selectivity to linear normal butyraldehyde. The conditions used are described in Example 10 below. The yield to the desired 1,10-decanedialdehyde with 150/1 TPP/Rh mole ratio catalyst was 54.7% while the yield to the desired product by this invention under the same experimental conditions was 74.8%. More significantly, the molar ratio of 1,10-decanedialdehyde to the sum of the isomeric branched decanedialdehyde products was 10.9/1 for the catalyst of this invention against 1.38/1 for the TPP/Rh catalyst. Table I lists examples of other ligand modified Rh oxo catalysts that were run under the conditions of Example 10 demonstrating the uniqueness of the present catalyst system.

DISCLOSURE OF THE INVENTION

The present ligands are compounds of the formula

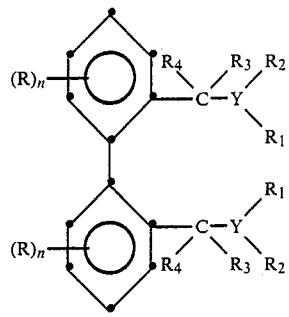

useful as ligands in hydroformylation and other reactions, wherein:

n is 1–4;

each R is independently selected from hydrogen, alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each $R_1$ and $R_2$ is independently selected from alkyl, aryl, aralkyl, alkaryl or cycloaliphatic;

each $R_3$ and $R_4$ is independently selected from hydrogen and the $R_1$ substituents;

each of the above alkyl groups or moieties is straight or branched chain of 1–20 carbons, each aryl group contains 6–10 ring carbons, and each cycloaliphatic group contains from 4–6 ring carbons; and each Y is independently selected from the elements N, P, As, Sb and Bi, with P being preferred.

The present hydroformylation process in its broad sense comprises contacting at least one $C_6$–$C_{10}$ diene in a reaction zone at a temperature of from about 20° C. to about 250° C. and a pressure of from about 15 psig to about 800 psig with syn gas ($H_2$, CO) and a catalyst comprising rhodium in chemical complex with one or more of the above ligands for a sufficient period of time to permit reaction of said olefin with said syn gas to form dialdehyde product.

If methanol is used in the above process as the solvent in the hydroformylation reaction, then the dialdehyde can be hydrogenated in the same solution. This is done by addition of Raney nickel to the autoclave followed by hydrogenation at 2000 psi $H_2$ at 100° C. for two hours. After recrystallization from dichloroethane, the 1,10-decanediol is obtained in 68% yield as a white crystalline solid. All the isomerization products are hydrogenated to n-nonanol under these conditions, and this compound is the major component left in the mother liquor after recrystallization o the diol.

Preferred of the present ligands are: 2,2'-bis-(diphenylphosphinomethyl)-1,1'-biphenyl (termed herein as BISBI); 2,2'-bis(dibenzylphosphinomethyl)-1,1'-biphenyl; 2,2'-bis(phenylbenzylphosphinomethyl)-1,1'-biphenyl; and 2,2'-bis(diisobutylphosphinomethyl)-1,1'-biphenyl. As a general statement of the actual chemical composition of the present active catalyst species in the reaction zone, the species preferably comprises rhodium complexed with (a) a ligand defined by the above structural formula in a molar ratio of ligand/Rh of about 1/1, (b) H in an atomic ratio of H/Rh of about 1/1, and (c) carbon monoxide in a molar ratio of CO/Rh of about 2/1.

Alternatively to the autoclave system the present process may also be carried out in conventional hydroformylation equipment such as in a gas sparged reactor such that the catalyst does not leave the reaction zone with the dialdehyde product which is taken overhead by the unreacted gases. The overhead gases are then chilled in a vapor liquid separator to condense out the aldehyde product, the gases being recycled to the reactor and the liquid product let down to atmospheric pressure for separation and purification by conventional techniques. A side draw from the reactor preferably is provided so that a small amount of the catalyst can be withdrawn at a desirable rate for more complete distillation and/or regeneration and returned to the reactor after the addition of make-up ligand thereto.

The rhodium catalyst component is charged preferably with solvent to the reactor through suitable pressurized pumping means, preferably in its soluble form, e.g., its carboxylate salts or mineral acid salts or the like well known to the art as disclosed, for example, in U.S. Pat. No. 2,880,241. Charged therewith or separately is one or more of the present modifying ligands in amounts such that the molar ratio of ligand to rhodium in the reactor is from about 1.0 to about 200 or more, preferably from about 2.0 to about 10.0, and most preferably from about 2.3 to about 4.0.

The process is particularly effective at pressures from about 15 to about 800 psig with from about 100 to about 400 psig being preferred, and from about 240 to about 280 psig being most preferred. The reaction temperatures can vary from about 20° to about 250° C., but preferably from about 50° to about 175° C. and most preferably from about 80° to about 150° C.

In the process, the syn gas is introduced into the reactor in a continuous manner by means, for example, of a primary compressor, and the ratio of hydrogen to carbon monoxide in the feed may be selected according to the particular diene being hydroformylated and the reaction conditions present, as is well known in the art. Generally, the molar ratio of hydrogen to carbon monoxide in the reactor is maintained within the range of about 0.5 to about 4.0, but it has been found in many hydroformylations that the rate of reaction as well as yield of the desired product may be increased by increasing the hydrogen to carbon monoxide molar ratio above 4.0, and up to about 10.0 or more. The syn gas preferably is present in a molar excess (total moles of $H_2 + CO$) with respect to the diene and the molar ratio varies typically from about 0.5 to about 20, preferably from about 1.2 to about 6. In a liquid overflow reactor, the above molar ratio may have a lower limit of about 0.02. The diene is fed to the reactor by means of suitable pumps capable of operating under substantial pressures, and the feed rates of the diene and syn gas are selected to maintain the above-recited molar ratios of these reactants in the reactor.

Any suitable solvent which does not adversely affect the hydroformylation process and which is inert with respect to the catalyst, olefin feed, syn gas and the hydroformylation products may be used. Inert solvents of this nature are well known to those skilled in the art and include benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents are those which are sufficiently high boiling to remain for the most part in the gas sparged reactor, and include 2,2,4-trimethyl-1,3-pentanediol monoisobutyrate (TMPDMI), and its isomers, and the by-products such as alcohols, esters, acetals, and hydroxyaldehydes produced in the hydroformylation reaction and retained as high boiling liquids at the bottom of the subsequent distillation columns.

The present process can be carried out with very small amounts of catalyst containing from about $1 \times 10^{-6}$ moles of rhodium (calculated as $Rh°$) per mole of olefin in the reactor zone. However, such low catalyst concentrations are not commercially desirable since the reaction rates are low. The upper catalyst concentration is essentially unlimited and appears to be dictated principally by the high cost of rhodium and the fact that no advantage is evident in the use of catalyst containing above about $1 \times 10^{-1}$ moles of rhodium per mole of olefin in the reactor zone. A concentration of from about $1 \times 10^{-5}$ moles to about $5 \times 10^{-2}$ moles of rhodium per mole of olefin is preferred, and from about $1 \times 10^{-4}$ to about $1 \times 10^{-2}$ is most preferred.

This invention will be illustrated further by the following examples although it will be understood that these examples do not limit the invention and are for purposes of illustration only. The synthesis of the present chelating diphosphine ligands is straightforward thus making them easily prepared in practical quantities. Below are given some of the synthetic routes available to prepare the ligands, the phosphorylation of 2,2'-bis(bromomethyl)-1,1'-biphenyl by alkali metal "M" phosphine anions being a particularly useful synthesis. Examples are given herein of the synthesis of the bis(diphenylphosphino), bis(phenylbenzylphosphino), and bis-(diisobutylphosphino) derivatives using this method (Reaction I). Likewise, the diphosphino chelate ligands may be prepared by the oxyphosphorylation of the above dibromo compound by its reaction with alkali metal salts of the phosphine oxide anion and subsequent reduction to the diphosphine chelating ligand (Reaction II) by any of a number of reducing agents such as lithium aluminum hydride.

Reaction I

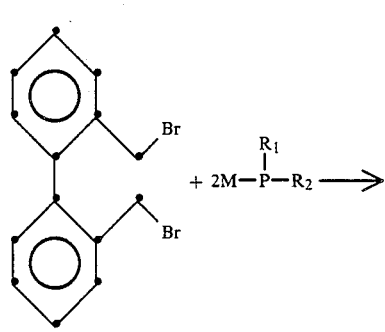

-continued
Reaction I

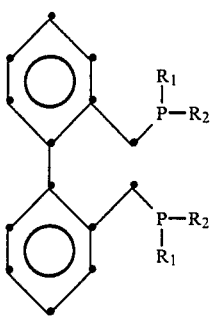

Reaction II

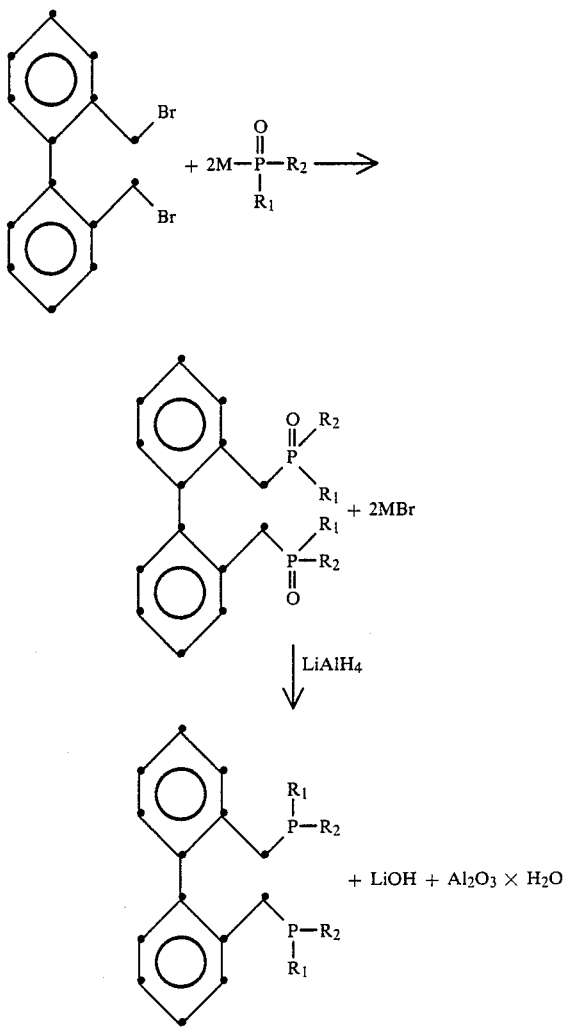

The above 2,2'-bis(bromomethyl)-1,1'-biphenyl intermediate is prepared in high yield from 2,2'-bis(hydroxymethyl)-1,1'-biphenyl by its reaction with PBr$_3$. The diol precursor is easily obtained in known manner by either standard catalytic hydrogenation or by lithium aluminum hydride reduction of diphenic acid. The diol is also easily prepared by reduction of 2,2'-bis(formyl)-1,1'-biphenyl, obtained by the high yield ozonolysis of phenanthrene in known manner.

All experimental procedures involving phosphines or organometallic compounds were run under an atmosphere of nitrogen using dry, deoxygenated solvents. Tetrahydrofuran (THF) was distilled under nitrogen from sodium/benzophenone ketyl. Chemical shifts for nuclear magnetic resonance (NMR) spectra are reported in parts per million ($\delta$) downfield from tetramethylsilane for $^1$H NMR spectra and relative to aqueous H$_3$PO$_4$ for $^{31}$P NMR spectra.

EXAMPLE 1

2,2'-Bis(hydroxymethyl)-1,1'-biphenyl

Lithium aluminum hydride (12.60 grams, 0.332 mol) and THF (175 ml) were placed in a dry 500 ml three-necked round-bottomed flask fitted with a condenser, addition funnel, nitrogen inlet, and magnetic stirrer. The mixture was cooled with an ice bath and diphenic acid (40.00 grams, 0.165 mol) in THF (100 ml) was added dropwise to the stirring mixture. After the addition was complete, the flask was removed from the ice bath and allowed to warm to room temperature. The reaction mixture was heated at reflux for 2 hours, then stirred overnight at room temperature. After cooling the mixture with an ice bath, water (12.6 ml) was added dropwise, followed by the successive dropwise addition of 15% aqueous sodium hydroxide (12.6 ml) and water (38 ml). The resulting yellow mixture was warmed to room temperature, and the solids were separated by vacuum filtration. The filtrate was placed on a rotary evaporator to remove the solvent. The remaining brownish-yellow solid was recrystallized from toluene-hexane to give 28.60 grams (81% yield) of light brown solid product, melting point 105° to 108° C.

$^1$H NMR (CDCl$_3$): $\delta$2.77 (br s, 2H, —OH); 3.95 (s, 4H, —CH$_2$—); 6.50–7.25 (m, 8H, aromatic).

EXAMPLE 2

2,2'-Bis(bromomethyl)-1,1'-biphenyl 2,2'-Bis(hydroxymethyl)-1,1'-biphenyl (25.00 grams, 0.117 mol) and methylene chloride (200 ml) were placed in a 500 ml round-bottomed flask equipped with a magnetic stirrer and an addition funnel with a CaCl$_2$ drying tube. The stirred mixture was cooled with an ice bath, and phosphorus tribromide (23.1 ml, 66.50 grams, 0.246 mol) was added dropwise from the addition funnel. After the addition was complete, the reaction mixture was removed from the ice bath and stirred overnight at room temperature. The mixture was again cooled with an ice bath, and water (35 ml) was added slowly. After stirring for 1 hour, additional water (75 ml) was added. The layers were separated in a separatory funnel, and the aqueous layer extracted twice with CH$_2$Cl$_2$. The combined organic layer was washed with saturated aqueous NaHCO$_3$ and water and was then dried with MgSO$_4$. The solvent was removed on a rotary evaporator to give 37.05 grams (93% yield) of light yellow solid which was suitable for use without further purification. The melting point was 85° C. to 88° C.

$^1$H NMR (CDCl$_3$): $\delta$4.10 (d, J=10 Hz, 2H, —CH—Br); 4.22 (d, J=10 Hz, 2H, —CH—Br); 6.92–7.53 (m, 8H, aromatic)

EXAMPLE 3

2,2'-Bis(diphenylphosphinomethyl)-1,1'-biphenyl

Diphenylphosphine (10.0 ml, 10.70 grams, 0.057 mol) was dissolved in dry THF (115 ml) under nitrogen in a 300-ml three-necked round-bottomed flask equipped with a magnetic stirrer, addition funnel, and condenser with a nitrogen inlet. The solution was cooled to about −70° C. with a dry ice/acetone bath and n-butyllithium (35.9 ml of a 1.6M solution in hexane, 0.057 mol) was added dropwise from the addition funnel. The orange solution was stirred 1 hour in the cold bath. A solution of 2,2'-bis(bromomethyl)-1,1'-biphenyl (9.30 grams, 0.027 mol) in THF (50 ml) was added dropwise from the addition funnel over about 20 minutes. The solution was allowed to stir overnight at room temperature and was then heated at reflux for 3 hours. Saturated aqueous NH$_4$Cl (about 50 ml) was added to the stirring solution at room temperature. Diethyl ether (75 ml) was added, and the layers were separated in a separatory funnel. The aqueous layer was extracted twice with diethyl ether. The combined organic solution was washed twice with water. The organic solvent was evaporated on a steam bath under a stream of nitrogen to give a thick, oily residue. The residue was recrystallized from ethanol/diethyl ether to give 10.64 grams (71% yield) of white solid, melting point 84° to 87° C.

$^1$H NMR (CDCl$_3$): δ3.15 (s, 4H, —CH$_2$—); 6.60–7.40 (m, 28H, aromatic). $^{31}$P NMR (CDCl$_3$): δ+9.

EXAMPLE 4

2,2'-Bis(diisobutylphosphinomethyl)-1,1'-biphenyl

Diisobutylphosphine (1.66 grams, 11.37 mmol) was dissolved in THF (25 ml) under nitrogen and cooled with a dry ice/acetone bath. n-Butyllithium (7.11 ml of a 1.6M solution in hexane, 11.37 mmol) was added dropwise to the stirring solution which was then allowed to stir for 1 hour in the cold bath. 2,2'-Bis(bromomethyl)-1,1'-biphenyl (1.89 grams, 5.55 mmol) in THF (10 ml) was added dropwise at −70° C. The solution was allowed to stir overnight at room temperature and was then heated at reflux for 1 hour. Saturated aqueous NH$_4$Cl was added to the solution at room temperature. Diethyl ether was added and the layers were separated in a separatory funnel. The aqueous layer was extracted twice with diethyl ether, and the combined organic solution was then washed twice with water. The solvent was removed on a steam bath under a stream of nitrogen. The oily residue was then placed on a Kugelrohr distillation apparatus to remove low boiling material at about 175° C. and 1 mm Hg leaving 1.88 grams (72% yield) of a thick orange glassy product.

$^1$H NMR (CDCl$_3$): δ0.65–1.67 (complex, 36H, aliphatic); 2.42 (s, 4H, benzylic); 6.67–7.30 (complex, 8H aromatic). $^{31}$P NMR (CDCl$_3$): δ+31.

EXAMPLE 5

2,2'-Bis(dibenzylphosphinomethyl)-1,1'-biphenyl Dioxide

Dibenzylphosphine oxide (6.93 grams, 30.1 mmol) and THF (100 ml) were placed in a 300-ml three-necked flask and cooled at −40° C. under nitrogen. n-Butyllithium (18.84 ml of a 1.6M solution in hexane, 30.1 mmol) was added dropwise from an addition funnel over about 10 minutes and the resulting yellow solution was stirred for 1 hour at −30° C. to −35° C. 2,2'-Bis(bromomethyl)-1,1'-biphenyl (5.00 grams, 14.7 mmol) in THF (20 ml) was added dropwise to the cold solution. When the addition was complete, the solution was warmed to room temperature and was then heated at reflux for 1.5 hours. Saturated aqueous NH$_4$Cl was added and the layers were separated. The aqueous layer was extracted twice with diethyl ether. The combined organic solution was washed with saturated aqueous NaCl. The organic solvent was evaporated on a steam bath under a stream of nitrogen to give a light browh solid. The product was recrystallized from acetone to give a first crop of 3.57 grams (38% yield) of white solid, melting point 203° to 205° C. No attempt was made to recover a second crop.

$^1$H NMR (CDCl$_3$): δ2.07–3.08 (complex, 12H, benzylic); 6.57–7.47 (complex, 28H, aromatic). $^{31}$P NMR (CDCl$_3$): δ−43.

EXAMPLE 6

2,2'-Bis(dibenzylphosphinomethyl)-1,1'-biphenyl

Chlorotrimethylsilane (4.1 ml, 32.2 mmol) was added to lithium aluminum hydride (1.22 grams, 32.2 mmol) in THF (20 ml) at −72° C. The mixture was removed from the cold bath, stirred 2 hours, and then cooled again at −35° C. A suspension of the above 2,2'-bis(dibenzylphosphinomethyl)-1,1'-biphenyl dioxide (3.40 grams, 5.32 mmol) in THF (45 ml) was added by cannula. The mixture was stirred 0.5 hour at −30° C., then overnight at room temperature. The reaction mixture was cooled in an ice bath and quenched by the successive, dropwise addition of water (1.2 ml), 15% aqueous NaOH (1.2 ml) and water (3.6 ml). The resulting mixture was filtered, and the solid was washed with diethyl ether. The filtrate was evaporated on the steam bath under a stream of nitrogen. The residual solid was heated in ethanol, then cooled and filtered to give 2.00 grams (62% yield) of white solid, melting point 163° to 167° C.

$^1$H NMR (CDCl$_3$): δ2.43 (s, 12H, benzylic); 6.50–7.17 (complex, 28H, aromatic). $^{31}$P NMR (CDCl$_3$): δ+9.5.

EXAMPLE 7

2,2'-Bis(benzylphenylphosphinomethyl)-1,1'-biphenyl

Benzyldiphenylphosphine (9.74 grams, 35.3 mmol) was dissolved in THF (100 ml) under nitrogen in a 250 ml three-necked round-bottomed flask equipped with a magnetic stirrer, thermometer, and condenser with a nitrogen inlet. A small amount of naphthalene (0.12 gram) was added followed by the addition of lithium metal (0.49 gram, 70.6 mmol) in small pieces. The mixture quickly became dark reddishbrown and was heated at 40° C. for 6 hours. t-Butyl chloride (2.29 grams, 24.8 mmol) was added dropwise at room temperature, and the mixture was stirred for 0.5 hour. 2,2'-Bis(bromomethyl)-1,1'-biphenyl (4.71 grams, 13.9 mmol) in THF (20 ml) was added dropwise, whereupon the color changed from dark red-brown to medium orange. The mixture was allowed to stir overnight at room temperaure and was then heated at reflux for 1 hour. Water (40 ml) was added and most of the THF was removed on the steam bath under a stream of nitrogen. The aqueous solution was extracted three times with diethyl ether. The combined organic solution was washed with water. The solvent was evaporated to leave an orange oily residue which was placed in a Kugelrohr distillation apparatus and heated at 220° C./1 mm Hg to remove low boiling components, leaving 9.20 grams of an orange glassy solid.

$^1$H NMR (benzene-d$_6$): δ3.28 (br s, 8H benzylic); 6.33–7.33 (complex, 28H, aromatic). $^{-}$P NMR (benzene-d$_6$): δ+10.

BEST MODES FOR CARRYING OUT THE INVENTION

EXAMPLE 8

Preparation of 1,10-Decanediol In Methanol

In a typical reaction according to the present invention, methanol (75 ml), Rh(CO)$_2$acac [rhodium (I) acetylacetonate dicarbonyl-commercially available] (18 mg, 0.07 mmol), BISBI (94 mg, 0.17 mmol), and 1,7-octadiene (1.5 g, 14 mmol) were loaded into a 300-ml stirred autoclave. The autoclave was sealed and purged with 50 psi CO/H$_2$ (1:1) at room temperature, then vented and pressurized with 200 psi CO/H$_2$ and heated at 100° C. After reaching 100° C., the autoclave was pressurized to 270 psi with CO/H$_2$. Additional CO/H$_2$ was added throughout the two-hour reaction period in order to maintain a constant temperature and pressure. After the two-hour reaction period and autoclave was cooled to room temperature and opened. A sample was taken for gas chromatographic analysis followed by addition of Raney nickel (2 g) to the autoclave. The above procedure was followed for the hydrogenation step using 1000 psi H$_2$ initial pressure, 100° C., and 2000 psi H$_2$ maintained for three hours.

The product as obtained from the autoclave was filtered to remove nickel, and the solvent evaporated to give a white solid. The solid was then recrystallized in ethylene dichloride to give 1.42 g (68% yield) of 1,10-decanediol as identified by NMR and GC mass spectroscopy. Gas chromatographic analysis (DB5 capillary column) of the methanol solution prior to hydrogenation indicated that the ratio of 1,10-decanedialdehyde to all other dialdehydes (by-products) was 15. The dialdehydes were identified by GC mass spectroscopy.

EXAMPLE 9

Hydroformylation of 1,7-Octadiene In Toluene

A solution was prepared under nitrogen, of toluene (89 ml), 1,7-octadiene (11.0 g, 0.10 mole), rhodium (I) acetylacetonate dicarbonyl (0.036 g, 0.14 mmole) and BISBI ligand (0.18 g, 0.0336 mmole) and charged to a 300 ml stainless steel Autoclave Engineers Magnedrive Autoclave under nitrogen. After sealing, the autoclave was pressured to 300 psig with 1/1 mole ratio of a hydrogen/carbon monoxide mixture (synthesis gas) and heated with stirring to 100° C. The autoclave was repressured to 300 psig with synthesis gas when the pressure dropped to 250 psig. The autoclave was kept at 100° C. for two hours and then cooled and vented of pressure. The product was analyzed on a medium bore 50 meter capillary gas chromatographic column with an F.I.D. detector using the toluene solvent as an internal standard. The conversion of 1,7-octadiene was 99.9% and the yield to 1,10-decanedialdehyde was 74.8%. The yields to other products are tabulated in Table I.

TABLE I

Batch Autoclave Hydroformylation of 1,7-Octadiene by Ligand Modified Rh Catalysts

| Run No. | Catalyst Ligand/Rh | Mole Ratio | % Conversion to 1,7-Octadiene | % Yield isomeric nonenal | % Yield H–CHO...CHO (branched) | % Yield 1,10-decanedialdehyde | Other isomeric C₁₀ dialdehyde | Mole Ratio 1,10-decanedialdehyde/Branched C₁₀ dialdehydes |
|---|---|---|---|---|---|---|---|---|
| 1 | BISBI/Rh | 2.4/1 | 99.9 | 18.35 | 0.12 | 6.52 | 74.81 | 0.21 | 10.9/1 |
| 2 | TPP/Rh | 150/1 | 99.9 | 5.73 | 4.80 | 33.41 | 54.71 | 1.35 | 1.38/1 |
| 3 | 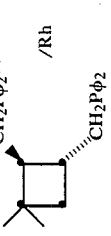 | 2.4/1 | 99.9 | 7.16 | 5.54 | 34.77 | 51.91 | 0.63 | 1.27/1 |
| 4 | 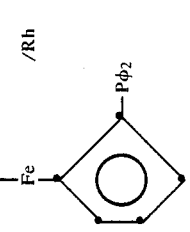 | 2.4/1 | 95.5 | 36.51 | 2.14 | 20.51 | 40.85 | 0.00 | 1.80/1 |
| 5 |  | 2.4/1 | 97.6 | 28.26 | 3.29 | 25.32 | 42.98 | 0.14 | 1.49/1 |
| 6 | Tri-n-octylphosphine/Rh | 5/1 | 99.9 | 1.78 | 11.17 | 44.02 | 42.38 | 0.65 | 0.76/1 |

All runs were carried out as in Example 9.
(a)Trans-1,2-bis(diphenylphosphinomethyl)-3,3-dimethylcyclobutane.

We claim:

1. A hydroformylation process for preparing dialydehydes from dienes comprising contacting at least one $C_6$-$C_{10}$ diene in a reaction zone at a temperature of from about 20° C. to about 250° C. and a pressure of from about 15 psig to about 800 psig with hydrogen, carbon monoxide, and a catalyst comprising rhodium in chemical complex with one or more ligands of the formula

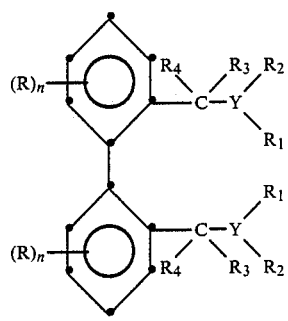

wherein:

n is 1-4;

each R is independently selected from hydrogen, alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each $R_1$ and $R_2$ is independently selected from alkyl, aryl, aralkyl, alkaryl or cycloaliphatic;

each $R_3$ and $R_4$ is independently selected from hydrogen and the $R_1$ substituents;

wherein each alkyl group or moiety is straight or branched chain of 1-20 carbons, each aryl group contains 6-10 ring carbon, and each cycloaliphatic group carbons from 4-6 ring carbons; and each Y is independently selected from the elements N, P, As, Sb and Bi;

for a sufficient period of time to permit reaction of said olefin with said carbon monoxide and hydrogen to form aldehyde product.

2. The hydroformylation process according to claim 1 wherein said reaction zone is operated at temperatures between about 80° C. and 150° C. and at pressures between about 100 psig and 400 psig, and the molar ratio of ligand to rhodium is from about 0.5 to about 200.

3. The hydroformylation process according to claim 2 wherein the molar ratio of said hydrogen to carbon monoxide is at least 0.5, and the total moles of hydrogen and carbon monoxide are present in said reaction zone in the ratio range of from about 0.02 to about 20 with respect to moles of said olefin.

4. The hydroformylation process according to claim 3 wherein said diene is selected from one or more of 1,7-octadiene, 1,5-hexadiene, or 1,9-decadiene.

5. The hydroformylation process according to claim 1 wherein said rhodium is present in said reaction zone in an amount between about $1 \times 10^{-6}$ to about $1 \times 10^{-1}$ moles per mole of said olefin present in said reaction zone.

6. The process of any one of claims 1-5 wherein said ligand is selected from: 2,2'-bis(diphenylphosphinomethyl)-1,1'-bisphenyl; 2,2'-bis(dibenzylphosphinomethyl)-1,1'-biphenyl; 2,2'-bis(phenylbenzylphosphinomethyl)-1,1'-bisphenyl; 2,2'-bis(diisobutylphosphinomethyl)-1,1'-biphenyl; or mixtures thereof.

7. The process of claim 6 wherein the diene is 1,7-octadiene.

8. The process of claim 7 wherein the molar ratio of ligand to rhodium is from about 2 to about 10.

9. The process of claim 6 wherein the molar ratio of ligand to rhodium is from about 2.3 to about 4.

10. The process of any one of claims 1-5 wherein the ligand is 2,2'-bis(diphenylphosphinomethyl)-1,1'-biphenyl.

* * * * *